(12) United States Patent
Liu et al.

(10) Patent No.: US 7,064,232 B2
(45) Date of Patent: Jun. 20, 2006

(54) HYDROPHOBIC MODIFIED DIQUATERNARY MONOMERS AND POLYMERS AS THICKENING AGENTS OF ACIDIC AQUEOUS COMPOSITIONS

(75) Inventors: Leo Z. Liu, Lawrenceville, NJ (US); Jeanne Chang, Madison, NJ (US)

(73) Assignee: Rhodia Inc., Cranbury, NJ (US)

( * ) Notice: Subject to any disclaimer, the term of this patent is extended or adjusted under 35 U.S.C. 154(b) by 50 days.

(21) Appl. No.: 11/006,143

(22) Filed: Dec. 7, 2004

(65) Prior Publication Data

US 2005/0124529 A1 Jun. 9, 2005

Related U.S. Application Data

(60) Provisional application No. 60/527,678, filed on Dec. 8, 2003.

(51) Int. Cl.
*C07C 69/54* (2006.01)
*C07C 69/527* (2006.01)
*C07C 233/09* (2006.01)

(52) U.S. Cl. ...................................... 560/222; 564/208
(58) Field of Classification Search ................ 560/222; 564/208
See application file for complete search history.

(56) References Cited

U.S. PATENT DOCUMENTS

| | | | |
|---|---|---|---|
| 3,968,037 A | 7/1976 | Morgan et al. ................. 210/47 |
| 4,172,066 A | 10/1979 | Zweigle et al. ............. 260/29.6 |
| 4,212,820 A | 7/1980 | Hotchkiss et al. ........... 260/561 |
| 4,495,367 A | 1/1985 | Dammann .................... 564/208 |
| 4,542,175 A | 9/1985 | Fink et al. ................... 524/516 |
| 4,563,292 A * | 1/1986 | Borchardt .................... 507/222 |
| 4,806,345 A | 2/1989 | Bhattacharyya .............. 424/70 |
| 5,114,600 A | 5/1992 | Biggin et al. ................. 252/86 |
| 5,603,926 A | 2/1997 | Matsumoto et al. ..... 424/70.15 |
| 6,271,192 B1 | 8/2001 | Verstrat et al. .............. 510/527 |
| 6,326,430 B1 | 12/2001 | Berte .......................... 524/555 |
| 2001/0016189 A1 | 8/2001 | Zhong et al. |

FOREIGN PATENT DOCUMENTS

| | | |
|---|---|---|
| EP | 0 395 282 B1 | 3/1995 |
| EP | 0 494 554 B1 | 3/1995 |
| JP | 02-274738 | * 11/1990 |
| WO | WO 99/06455 | 2/1999 |
| WO | WO 99/20725 | 4/1999 |
| WO | WO 01/57171 | * 8/2001 |
| WO | WO 01/05920 | * 1/2005 |

OTHER PUBLICATIONS

Joynes, D.; Sherrington, D. C. Polymer, vol. 37 No. 8, pp. 1453-1462, 1996.

* cited by examiner

*Primary Examiner*—John R. Hardee (57) ABSTRACT

The invention relates to the preparation of hydrophobic modified diquaternary cationic monomers and their copolymer as well as the use such monomers and copolymers as thickening agents/rheology modifiers for acidic compositions. The hydrophobic modified diquaternary cationic monomer having the general formula:

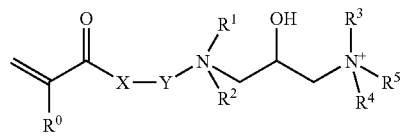

wherein X is selected from O, NH, or NR; Y is any alkyl, alkylene with or without heteroatoms, and $R^0, R^1, R^2, R^3, R^4$, which are identical or different, are selected from C1–C4 alkyl groups, R is selected from any alkyl group with or without heteroatoms, and $R^5$ is a hydrphobe having an alkyl chain of more than 4 atoms.

7 Claims, 4 Drawing Sheets

HYDROPHOBIC MODIFIED DIQUATERNARY MONOMERS AND POLYMERS AS THICKENING AGENTS OF ACIDIC AQUEOUS COMPOSITIONS

This patent application claims priority from U.S. provisional patent application Ser. No. 60,527/678 filed on Dec. 8, 2003.

FIELD OF THE INVENTION

The invention relates to the preparation of hydrophobic modified diquaternary cationic monomers and their copolymer as well as the use such monomers and copolymers as thickening agents/rheology modifiers for acidic compositions.

BACKGROUND OF THE INVENTION

Rheological properties of home care formulations are often managed with the use of natural or synthetic polymers. Frequently, the formulator is looking for a liquid formulation with a shear thinning viscosity profile either for aesthetic purposes of providing the impression of a thick formulation rich in actives, and/or for performance benefits such as facilitating cling to a vertical surface which might allow additional contact time for a detergent to perform its cleaning action. Some of the most commonly used polymers are high molecular weight polyacrylates, alkali swellable latex, modified celluloses, guar gum, and xanthan, all of which have found widespread use in laundry and dish liquids plus some hard surface cleaners.

While most compositions for home care have a neutral to alkaline pH, there are a couple of applications where formulas may be highly acidic. Specifically, these applications are toilet bowl cleaners and fabric softeners. In the case of toilet bowl cleaners, there is a strong interest in controlling the rheology, since cling time to the toilet bowl affects the overall performance of the product. In the case of fabric softeners, the desire to thicken the formulation is more often for aesthetics, as consumers are accustomed to fabric softener products which have a high viscosity. However, both of these products may be formulated to pHs as low as 2 or 3, and few polymers are effective at extremely low pH conditions. In the case of most polysaccharides, highly acidic conditions degrade the polymers, such that with time the viscosity may drop off significantly. Xanthan and succinoglycan gum are generally recommended for low pH formulations, but even they are not always effective at the very low pH range. Of the synthetic polymers, most are designed to viscosify at neutral to alkaline conditions, and are not effective at acidic conditions. For example, with polyacrylates and the alkali swellable latexes, low pH conditions will neutralize the carboxylic acid function, rendering the polymer often insoluble or at minimum effectiveness in low pH conditions. These thickeners also either lose their thickening property or cause precipitation of the formulation.

In addition to the potentially very low pH conditions of toilet bowl cleaners and fabric softeners, another constraint in chemistries developed for rheology management is the presence of quaternary surfactants. While laundry and dish liquid detergents are anionic surfactant based. Fabric softeners are commonly made up of ester quats, and toilet bowl cleaners may often contain quaternary surfactants for antibacterial claims. The level of quats in the two types of formulations are significantly different. Fabric softeners may contain anywhere between 10–20wt % ester quats, while quaternary ammonium type surfactants for antibacterial claim are generally added at less than 0.5 wt %. However, the consequence of the presence of quaternary surfactants in the formulation is the same for both formulations, namely, that many typical rheological modifiers will be incompatible due to their anionic charge.

Polymers, and especially copolymers, comprising cationic units are useful in various applications. In formulations, for example in home care formulations, personal care formulations, or formulations used in oil-field industry, the cationic units may interact with other compounds, such as surfaces, surfactants or active ingredients, and provide specific properties. Various polymers and copolymers comprising cationic units are used. Some properties and/or structures of formulation can be tuned by using copolymers comprising several cationic units. Developing new monomers and therefore new polymers or copolymers allows for development of new formulations with either environment protection improvements, or of course new and improved properties or functions.

Copolymers comprising units that comprise two cationic groups (hereafter referred to as di-cationic units), and preparation thereof, have been described, and are used for example in home care formulations such as hard surface cleaning formulations.

Hydrophobic modified cationic monomers have been described by Gipson et al,[1] and reported recently by Joynes et al[2]. These are surfactant monomers that can be copolymerized, imparting the polymer with both the cationicity and hydrophobicity. Diquaternary monomer without hydrophobes was prepared by Dammann[3]. It is enviable that a hydrophobically modified diquaternary and multi-quaternary monomers would provide its polymer or its copolymer unique properties, such as complex formation with surfactants and/or self-association as thickeners.

[1] Gipson, R. M.; Hotchkiss, P.; Nieh, E. C. Y. (Texaco) U.S. Pat. No. 4,212,820 (1980)

[2] Joynes, D.; Sherrington, D. C. Polymer, 37(8), 1453, 1996

[3] Dammann, L. G. (Celanese) U.S. Pat. No. 4,495,367 (1985)

There is an increasing demand for thickeners in acidic compositions and/or compositions of mostly cationic surfactants. There are few examples of thickeners for acidic media published in the literature and/or commercially available. For example, U.S. Pat. No. 6,326,430 describes a cross-linked poly(methacryloxyethyltrimethylammonium) salt as thickening agent for aqueous laundry softeners which comprise cationic surfactants as active ingredients and toilet cleaners[4]. The polymer was synthesized in w/o emulsion and cross-linked with N,N'-methylenebisacrylamide. Similar polymers were also described in various patents.[5] Separately, U.S. Pat. No. 6,271,192 describes a thickener latex of a polymer from ethyl acrylate, dimethylaminoethyl methacrylate and an associative monomer. The latex is a microgel cross-linked by diallylphthalate.[6] A similar polymer was synthesized by precipitation polymerization in an organic solvent, where a polymer microgel of dimethylaminoethyl methacrylate, vinylpyrrolidone and steryl acrylate was cross-linked by tripropylene glycol diacrylate.[7] A patent was filed recently for a cross-linked hydrogel of vinylpyrrolidone and dimethylaminopropyl methacrylamide. This hydrogel was prepared by solution polymerization and was demonstrated to show thickening property upon acidification.[8]

[4] Berte, F. U.S. Pat. No. 6,326,430 (2001). Berte, F.; Polotti, G. WO 99/20725 (1999); WO/99/06455 (1999).

[5] U.S. Pat. No. 3,968,0387; U.S. Pat. No. 4,806,345; EP 395,282; EP 494,554; U.S. Pat. No. 4,172,066; U.S. Pat. No. 5,114,600; U.S. Pat. No. 4,542,175

[6] Verstrat, D. W.; Maxim, J. S.; Rosie, J. U.S. Pat. No. 6,271,192 B1

[7] Matsumoto, K.; Uchiyama, Y.; Kambe, T. Nanba, T. Okuda, Y. (Osaka Yuki Kagaku Kogyo Kabushiki Kaisha & Shiseido Company) U.S. Pat. No. 5,603,926 (1997)

[8] Zhong, Y.; Jachowicz, J.; Wolf, P. F. McMullen, R. L. Jr. (ISP), US2001/0016189 A1 (2001)

In summary, the cationic polymers described in the current arts as thickener for acidic formulations are almost exclusively chemically cross-linked. The cross-linking polymer network is necessary for the viscosity boost. However, the viscosity obtained is less stringy. There are still needs for better products that can thicken the acidic/cationic compositions at a low dose. It is also desirable to provide a thickening polymer that can be prepared without a cross-linking monomer. Such a polymer would have improved hydration speed and improved viscosity, i.e., less stringy.

BRIEF SUMMARY OF THE INVENTION

A first aspect of the invention relates to a hydrophobic modified diquaternary cationic monomer having the formula (I):

wherein X is selected from O, NH, or NR; Y may be any alkyl, alkylene with or without heteroatoms, and $R^0$, $R^1$, $R^2$ $R^3$, $R^4$ are alkyl groups preferably C1–C4 alkyl. R is any alkyl group with or without heteroatoms. $R^5$ is a hydrphobe that has alkyl chain of more than 4 atoms.

A second aspect of the invention relates to a process for preparing the monomer compound of formula (I) via the following scheme:

wherein X is selected from O, NH, or NR; Y may be any alkyl, alkylene with or without heteroatoms, and $R^0$, $R^1$, $R^2$ $R^3$, $R^4$ are alkyl groups preferably C1–C4 alkyl. R is any alkyl group with or without heteroatoms. $R^5$ is a hydrphobe that has alkyl chain of more than 4 atoms.

In a third aspect of the invention there is provided a copolymer of the hydrophobic modified diquaternary cationic monomer having a general formula (II):

wherein $R=C_{12}H_{23}$ or $C_{18}H_{37}$.

In a fourth aspect of the invention there is provided a method of synthesizing the copolymers of formula (II) via the following scheme.

wherein $R=C_{12}H_{23}$ or $C_{18}H_{37}$.

In yet a fifth aspect of the invention relates to the use of such hydrophobic modified diquaternary cationic monomers and their copolymers as a thickening agent for acidic compositions.

DETAILED DESCRIPTION OF THE INVENTION

As used herein the term "home care formulation" shall include but is not limited to general household cleaning products for example, toilet bowl cleaners, laundry detergents, fabric softeners, dishwashing liquid, and bathroom cleaner.

Hereinafter the term "diquaternary" may be referred to as "diquat" or "diquats" as is generally understood in the industry.

New hydrophobic cationic diquaternary monomers are described herein. The copolymers are synthesized from these monomers without cross-linking monomers. The products so obtained exhibit very good thickening properties in acidic formulations.

Monomer Compound

A hydrophobically modified cationic diquaternary monomer compound according to the first aspect of the invention, preferably has a general formula (I):

(I)

wherein X is selected from O, NH, or NR; Y may be any alkyl, alkylene with or without heteroatoms, and $R^0$, $R^1$, $R^2$ $R^3$, $R^4$ are alkyl groups preferably C1–C4 alkyl. R is any alkyl group with or without heteroatoms. $R^5$ is a hydrphobe that has alkyl chain of more than 4 atoms.

Synthesis of Monomer Compound

The hydrophobically modified cationic diquaternary monomer compound described above was prepared by using commercially available materials as shown in Scheme 1.

Scheme 1 wherein X is selected from O, NH, or NR; Y may be any alkyl, alkylene with or without heteroatoms; $R^0$, $R^1$, $R^2$, $R^3$, and $R^4$ are alkyl groups preferably $C_1$–$C_4$ alkyl; R5 is alkyl, preferably a hydrophobes, and more preferably an alkyl, aromatic with four or more Carbons. R is any alkyl group with or without heteroatoms.

The monomer ($C_{12}$ or $C_{18}$-Diquat) can be prepared by reacting commercially available dimethylaminopropyl-methacrylamide (DMAPMA) with hydrophobic modified chlorohydrin (3-chloro-2-hydroxypropyl-dimethyldodecy-lammonium chloride, known as Quab-342 or 3-chloro-2-hydroxypropyl-dimethylstearylammonium chloride, i.e. Quab 426, available from Degussa) at equal molar amounts in aqueous solution. The reactions are preferably carried out at about 60° C. and while purging with air. No extra inhibitor of MEHQ is required beyond the amount carrying from DMAPMA. In the case of $C_{18}$-Diquat, the reactant Quab 426 preferably contains a suitable amount of 1,3-propanediol (more preferably from about 23% to about 28%) which is utilized as a solvent for the reaction. The products from these reactions were confirmed by high performance liquid chromatographic (hereinafter "HPLC") analysis.

Copolymers

A copolymer of the hydrophobically modified cationic diquaternary monomer compound according to the second aspect of the invention, preferably has a general formula (II):

(II)

wherein R=$C_{12}H_{23}$, or $C_{18}H_{37}$.

Synthesis of Copolymers

Any suitable monomer may be used for polymerization of the diquaternary cationic monomers to produce copolymers in accordance with the invention. Vinyl monomers, such as dimethylaminoethyl methacrylate (DMAEMA), dimethylaminopropyl methacrylamide (DMAPMA), N-vinylpyrrolidone (NVP) as shown in Scheme 2, are known building blocks for thickeners of an acidic composition or composition mainly consisting of cationic surfactants or/and cationic polymers. Thus DMAEMA, DMAPMA and NVP are preferred for copolymerization with the hydrophobically modified diquaternary cationic monomers.

Any suitable polymerization process may be used. For example, the polymerizations may be carried out in solution, in suspension, or in bulk. It has been discovered that suspension polymerization in aqueous sodium carbonate/bicarbonate is preferred. The suspension polymerization was found suitable for producing micro-beads of water soluble polymer in an aqueous phase.

1. Solution Polymerization

As discussed above, the diquaternary monomer may be copolymerized at about 0.1 to 15% and more preferably about 5% by weight with a suitable vinyl monomer or combinations thereof, for example vinylpyrrolidone (VP) and DMAPMA, to yield a cationic thickening polymer in accordance with the invention. Any suitable solvent may be used to carry out the polymerization. For example, ethanol, toluene, t-butanol, water, and combinations thereof may be used for polymerization, with water being preferred and a mixture of water and t-butanol being more preferred.

2. Suspension Polymerization in Aqueous Salt Solution

Any suitable suspension solution may be used. Suitable solutions include sodium sulfate, sodium carbonate, and sodium bicarbonate. The solution should also preferably include a surfactant emulsifier and a polymer-bead stabilizer. Micro-beads of the copolymer may be obtained by using an amphoteric surfactant, for example, sodium lauroamphoacetate commercially available as MIRANOL ULTRA L-32/PG from Rhodia Inc., and/or poly-methacrylamidopropyltrimethylammonium chloride (poly(MAPTAC).

3. Bulk Polymerization

Another favorable polymerization process is bulk polymerization, which can be carried out in an intruder of reactor. This could be achieved by similar reaction conditions to the polymer beads of suspension polymerization.

Diquaternary Monomers and Copolymers as Thickening Agents

The invention also relates to the use of the aforedescribed copolymers of diquaternary cationic monomers as thickening agents. The diquaternary cationic monomers and copolymers of the invention are particularly useful in acidic surfactant formulations. The diquat polymers may be used as rheology modifiers to increase viscosity in acidic surfactant formulations without affecting the compatibility or appearance of the formulations. The diquat polymers are particularly useful as rheology modifiers in highly acidic home care formulations including toilet bowl cleaners and fabric softeners. The diquat polymers of the invention are also particularly useful in formulations containing from about 10 to about 20% ester quats.

Some illustrative but non-limiting examples are provided hereunder for the better understanding of the invention.

EXAMPLES

I. Synthesis of Hydrophobically Modified Diquaternary Monomer

The hydrophobically modified cationic diquats were prepared by using commercially available materials (Scheme A)

In general, $C_{12}$ or $C_{18}$-Diquaternary monomer was obtained by reacting dimethylaminopropylmethacrylamide (DMAPMA) with hydrophobic modified chlorohydrin (3-chloro-2-hydroxypropyl-dimethyldodecylammonium chloride, i.e. Quab-342 or 3-chloro-2-hydroxypropyl-dimethylstearylammonium chloride, i.e. Quab 426, commercially available from Degussa) at equal molar amounts in aqueous solution. The reactions were carried out at 60° C. and under air purging. No extra inhibitor of MEHQ was added besides the amount carrying from DMAPMA. In the case of $C_{18}$-Diquats, the reactant Quab 426 contained 23–28% of 1,3-propanediol, which was utilized as a solvent for the reaction. The products from these reactions were confirmed by HPLC analysis. The monomer solution at 50% active was a liquid at the reaction temperature, but would turn to a waxy gel at room temperature.

Preparation of $C_{12}$-Diquaternary. For these examples, particularly, a 40% solution of 3-chloro-2-hydroxypropyl-dimethyldodecylammonium chloride known as Quab-342 commercially available from Degussa, (42.75 parts) was added slowly to Dimethylaminopropylmethacrylamide, DMAPMA, (8.51 parts) at room temperature. The mixture was then heated to 60° C., and maintained at this temperature for 2 hours. The product was obtained as a waxy gel upon cooling to room temperature.

Preparation of $C_{18}$-Diquaternary. For these examples particularly, a 40% solution of 3-chloro-2-hydroxypropyl-dimethyldodecylammonium chloride known as Quab-426 commercially available from Degussa, (53.25 parts) was added slowly to Dimethylaminopropylmethacrylamide, DMAPMA (8.51 parts) at room temperature. The mixture was then heated to 60° C. and maintained at this temperature for 2 hours. The product was obtained as a waxy gel upon cooling to room temperature.

II. Synthesis of Copolymers

Vinyl monomers, such as dimethylaminoethyl methacrylate (DMAEMA), dimethylaminopropyl methacrylamide (DMAPMA), N-vinylpyrrolidone (NVP) shown in Scheme B, are known building blocks for thickeners of an acidic composition or composition mainly consisting of cationic surfactants or/and cationic polymers. Thus DMAEMA, DMAPMA and NVP were chosen to copolymerize with the hydrophobically modified diquaternary monomers. The polymerizations were carried out in solution, in suspension, or in bulk.

Scheme B

DMAPMA

DMAEMA

VP

Aqueous Polymerization. N-vinylpyrrolidone (24.2 g), dimethylaminopropyl-methacrylamide (24.3 g) and $C_{18}$-Diquat 50% (4.78 g) and water (200.0 g) were added into a 500 ml flask equipped with mechanic stirrer, thermometer and nitrogen inlet. The mixture was heated to 70° C. under mechanical agitation and nitrogen purge. Both the agitation and purge were maintained throughout the reaction. TRIGANOX 25 C75, commercially available from Akzo Nobel, was introduced to the reaction at 70° C. after at least one hour of nitrogen purging. The reaction was kept at 70° C. for 2 hours, then 0.10 g TRIGANOX 25 C75 was added again. The batch became very viscous 15 minutes after the second shot of initiator and had to be diluted with 200 g of water. The reaction was held for another hour at 70° C. and then terminated. The batch was still very viscous and had to be diluted with isopropanol at a weight ratio of 4:1 in order to be taken out of the reactor. The polymer so prepared showed thickening at acidic pH.

The $C_{18}$-Diquaternary monomer was copolymerized at 5% by weight with vinylpyrrolidone (VP) and DMAPMA to yield a cationic thickening polymer. The polymer of 47.5: 47.5:5 (by weight, lot R0309-146) of VP:DMAPMA:$C_{18}$-Diquaternary monomer was prepared in water. Due to the viscosity build-up, continuous dilution with water was applied. The final polymer product, at 6–7% in IPA and water, showed thickening upon acidification and further thickening in the presence of non-ionic surfactants. The thickening properties of this preliminary sample are demonstrated in the home care formulation examples that will be described afterwards.

Polymerization in Butanol and Water. The reaction was carried in a similar way as aqueous polymerization, but with the addition of tert-butanol/n-butanol to reduce the viscosity. The charges are listed in Table 1. The following is a typical example showing how a polymer was synthesized. N-vinylpyrrolidone (12.3 g), dimethylaminopropylmethacrylamide (12.4 g) and $C_{18}$-Diquat, 50% (2.4 g), n-butanol (45.0 g) and water (45.0 g) were added into a 500 ml flask equipped with mechanic stirrer, thermometer and nitrogen inlet. The mixture was heated to 70° C. under mechanical agitation and nitrogen purge. Both the agitation and purge were maintained throughout the reaction. The batch was cloudy at room temperature and then turned clear at 65° C. TRIGANOX 25 C75 (0.25 g) was introduced to the reaction at 70° C. and after purging for at least 1 hr. The batch became viscous and cloudy 10 minutes after the initiator addition. The reaction was held at 69–70° C. for 4 hours, and then 0.15 g TRIGANOX 25 C75 was introduced and the batch was held for 1 hr. As the batch was too viscous, 10 g of n-butanol was added together with 0.15 g TRIGANOX 25 C75. The mixture was held at 70° C. for 45 minutes to yield a polymer solution that could be poured out of the reactor.

Suspension polymerization in aqueous salt solution. It was discovered that VP, DMAPMA, and DMAEMA as well as their copolymer are not easily soluble in a concentrated electrolyte solution. Thus, suspension polymerization of VP/DMAPMA/C18Diquaternary monomer was investigated in the presence of sodium sulfate, sodium carbonate, or sodium bicarbonate together with a surfactant emulsifier and a polymer-bead stabilizer (Table 2). Micro-beads of the copolymer were obtained by using an amphoteric surfactant (MIRANOL ULTRA L-32/PG commercially available from Rhodia, i.e. sodium lauroamphoacetate) and poly(methacrylamidopropyltrimethylammonium chloride) (poly(MAPTAC). However, the use of salt was carefully chosen in order to produce water soluble polymer beads.

As shown in Table 2, when sodium sulfate was used as the salt, the reaction would result in insoluble polymeric microbeads. These insoluble micro-beads were most likely caused by the polymerization at alkaline conditions. Therefore, sodium carbonate was used instead, so that the residual carbonate could help to unpack the beads. It is believed that the release of carbon dioxide would generate internal pressure in the beads to blow them up, when the polymer is exposed to acidic solution. Samples with various amount of C-18 Diquats were prepared with the amphoteric surfactant and sodium carbonate. Samples of DMAPMA were shown to give very low viscosity. This was most likely due to the incomplete swelling/unpacking of the micro-bead particles. Thus the process was further improved by incorporating $HCO_3$ to the polymer, which was utilized as the counter-ion for the tertiary amine function. Therefore, more carbonate could be retained inside the beads for dissolution. This was accomplished by carrying the suspension polymerization in sodium bicarbonate or its mixture with sodium carbonate. The addition of sodium bicarbonate also helped to further reduce the alkalinity of the reactants. These samples showed much better solubility and faster dissolution in acidic solution. Selective samples were evaluated in thickening toilet bowl cleansers and fabric softeners. In some cases, the samples demonstrated superior thickening properties over existing commercial products.

The following is a typical example of how the charges in Table 2 were synthesized. N-vinylpyrrolidone (30.0 g), dimethylaminopropylmethacrylamide (30.06 g) and $C_{18}$-Diquat, 50% (6.03 g), sodium bicarbonate (25.0 g), MIRANOL ULTRA L-32 (3.07 g), Poly(MAPTAC) 33% of viscosity 53,000 cps (6.66 g), water (150.0 g) and AIBN (0.15 g) were added into a 500 ml flask equipped with mechanic stirrer, thermometer and nitrogen inlet. Both the agitation and purge were maintained throughout the reaction. The mixture was heated to 70° C. and the temperature was maintained for 3 hours. Then AIBN (0.15 g) was added and the reaction was held for an additional hour. A second initiator, Vazo V56, 0.15 g was introduced. The temperature was increased to 80° C. and held for 2 hr. The polymer beads so obtained were filtered and dried in Vacuum at 50–60° C. Total yield 67.0 g.

TABLE 1

Polymerization of $C_{18}$-Diquat, DMAPMA and NVP in Butanol and Water[9]

| Trial # | $C_{18}$-Diquat, 50% | DMAPMA | NVP | Butanol | Water | 36.5% HCl | product |
|---|---|---|---|---|---|---|---|
| 187 | 2.0 | 10.0 | 10.0 | 20.0[10] | 65.0 | 0 | gel |
| 188 | 3.0[11] | 17.0 | 11.5 | 30.0[12] | 90.0 | 0 | gel |
| 191 | 2.4 | 10.6 | 10.3 | 20.0[10] | 60.0 | 0 | gel |
| 193 | 2.2 | 10.0 | 10.4 | 55.0[12] | 55.0 | 0.5 | milky |
| 194 | 2.1 | 10.1 | 10.3 | 40.0[12] | 40.0 | 0.5 | OK |
| 202 | 2.4 | 12.4 | 12.3 | 45.0[12] | 45 | 1.0 | OK |

[9]Polymerization was initiated with 0.1 part of TRIGANOX 25 C75 at 70 to 75° C.
[10]t-butanol was used
[11]Vazo 56 was used instead of TRIGANOX 25 C75
[12]n-butanol was used

TABLE 2

Suspension Polymerization in Aqueous Salt Solution

| Lot # | $C_{18}$ Diquat, 50% | DMAPMA | DMAEMA | VP | salt | MIRANOL L32 | Poly (MAPTAC), 33%, 53,000 cps | water | AIBN | Vazo 56 | Beads solubility in acidic solution |
|---|---|---|---|---|---|---|---|---|---|---|---|
| R0309-204 | 3.12 | 15.51 | — | 15.03 | 10.0/ $Na_2SO_4$ | 1.16 | 3.57 | 90.0 | 0.30[13] | 0.15 | no |
| R0309-205 | 4.03 | 20.0 | — | 20.0 | 17.1/ $Na_2CO_3$ | 2.04 | 6.38 | 120.0 | 0.40 | 0.10 | swellable |
| R0209-206 | 3.61 | 30.12 | — | 30.13 | 25.0/ $Na_2CO_3$ | 2.91 | 7.28 | 150.0 | 0.30 | 0.15/ | swellable |
| R0309-207 | 1.02 | 25.14 | — | 24.95 | 21.1/ $Na_2CO_3$ | 2.69 | 6.11 | 125.0 | 0.25 | 0.125 | swellable |
| R0309-208 | — | 30.32 | — | 30.08 | 25.0/ $Na_2CO_3$ | 3.35 | 7.38 | 150.0 | 0.30 | 0.15 | — |
| R0376-2 | 3.60 | — | 30.0 | 28.2 | 25.0/ $Na_2CO_3$ | 2.91 | 6.00 | 150.0 | 0.15 | 0.15 | soluble |
| R0376-6 | 6.01 | 30.0 | — | 30.0 | 15.0/ $Na_2CO_3$[14] | 3.00 | 5.41 | 150.0 | 0.15 | 0.15 | Soluble at >90° C. |
| R0376-8 | 6.03 | 30.06 | — | 30.0 | 25.0/ $NaHCO_3$ | 3.07 | 6.66 | 150.0 | 0.15 | 0.15 | Soluble |
| R0376-9 | 5.99 | 30.0 | — | 30.0 | 18.2/ $NaHCO_3$[15] | 4.15 | 6.80 | 120.0 | 0.15 | 0.15 | soluble |

TABLE 2-continued

Suspension Polymerization in Aqueous Salt Solution

| Lot # | $C_{18}$ Diquat, 50% | DMAPMA | DMAEMA | VP | salt | MIRANOL L32 | Poly (MAPTAC), 33%, 53,000 cps | water | AIBN | Vazo 56 | Beads solubility in acidic solution |
|---|---|---|---|---|---|---|---|---|---|---|---|
| R0376-10 | 6.06 | 15.15 | 15.15 | 30.15 | 15.15/ NaHCO$_3$[16] | 2.88 | 6.15 | 150.0 | 0.15 | 0.15 | soluble |

[13]TRIGANOX 25 C75 is used instead of AIBN
[14]10.0 part of NaHCO$_3$ was added
[15]4.15 parts of Na$_2$CO$_3$ was added
[16]18.0 parts of Na$_2$CO$_3$ was added

III. Usage in Home Care Formulations

3.1 Materials

Polymers were screened in either a quaternary surfactant based fabric softener and/or a toilet bowl cleaner. The products used for screening and their "as is" pH were as follows:

TABLE 3

"As Is" pH

| Product | pH |
|---|---|
| RHODAQUAT T diluted to 10% active[17] | 3.3 |
| Downey Fabric Enhancer[18] | 3.85 |
| Unilever fabric softener base[19] | 2.84 |
| ROBIJN[20] | 2.78 |
| Comfort[21] | 2.84 |
| Clorox toilet bowl cleanser base material[22] | 2.37 |

[17]Commercially available from Rhodia Inc.
[18]Commercially available from Procter & Gamble Co.
[19]Commercially available from Unilever
[20]Commercially available from Unilever
[21]Commercially available from Unilever
[22]Commercially available from Clorox Several random as well as diblock copolymers were screened, in addition to some identified commercially available competitor products. Comparisons were also made to some viscoelastic surfactant systems. A summary of the products screened and in which particular kind of formulation is shown in the Table 4 below.

TABLE 4

Product Summary[23]

| | Fabric Softener | Toilet Bowl Cleaner |
|---|---|---|
| Random Copolymers | | |
| VP:MAPTAC (1:9) | X | |
| VP:MAPTAC (3:7) | X | |
| AA:MAPTAC (1:9) | X | |
| AA:MAPTAC (3:7) | X | |
| VP:PADAMQUAT (8:2) | X | |
| HEA:DADMAC (1:9) | X | |
| CLA-STA FS[24] | X | |
| ALKAFLOC EC-752M[25] | X | X |
| PAA w/PEO grafts (01VTA105) | X | |
| VP:DMAPMA:C18 DIQUAT (47.5:47.5:5) | X | X |
| Block Copolymers | | |
| PAA:PAM (1k/10k) | X | |
| PAA:PAM (1k/1k) | X | |
| PAA:PAM (1k/5k) | X | |
| VP:PADAMQUAT (50k/10k) | X | |
| Misc Rhodia Technologies | | |
| Jaguar HP105[26] | X | X |
| VES (XE-90-C22 betaine) | X | X |
| Competitive Products | | |
| Alcogum L-511[27] | X | X |
| Alcogum L-520[28] | X | X |
| Acrysol RM-825[29] | X | X |
| SNF DP200[30] | X | X |
| 3V Sigma CN[31] | X | X |
| 3V Sigma CR[32] | X | X |

[23]MAPTAC, methacryloylaminopropyltrimethylammonium chloride; ADAMQUAT, (2-methacryloyloxy)ethyltrimethylammonium chloride; HEA, hydroethylacrylate; DADMAC, diallydimethylammonium chloride; PAA, polyacrylic acid; PVP, poly(vinylpyrrolidone), PADAMQUAT, poly [(2-methacryloyloxy)ethyltrimethylammonium chloride]; PEO, polyethylene oxide; PAM, polyacrylamide
[24]Commercially available from Rhodia Inc.
[25]Commercially available from Rhodia Inc.
[26]Commercially available from Rhodia Inc.
[27]Commercially available from National Starch & Chemical Company
[28]Commercially available from National Starch & Chemical Company
[29]Commercially available from Rohm & Haas
[30]Commercially available from SNF
[31]Commercially available from 3V Sigma
[32]Commercially available from 3V Sigma

3.2 Sample Preparation

The form of each polymer received, dictated the manner in which it was formulated into the existing formulations. Specifically, it was preferable where possible to test the polymer by adding it into the formula directly without diluting the overall formula concentration. However, in cases where the polymer was received in solution at less than 100% active, or in cases where it was difficult to mix in a 100% active polymer in solid form, it was necessary to dilute the formula to more or less degree in order to mix it into the formulation.

Where possible the chemistries were tested at 1% in the formulation. In cases where the chemistry showed promise, the concentration level was reduced to determine the minimum level where performance was still observed. In all cases, once the chemistry to be screened was incorporated into the formula, the pH was measured and compared to the pH of the formula without the chemistry. If there was any change in the pH due to the incorporation of the chemistry, the pH was readjusted so as to match the pH of the original formulation.

3.3 Chemistry Evaluation

Chemistries were initially evaluated based upon the appearance of the formula once the chemistry was incorporated. Such aspects as compatibility, turbidity, and visual observation of viscosity were all noted and compared to the control, e.g. the formulation without the chemistry addition. In cases where it appeared that the polymer did not affect the overall appearance of the formulation, but did appear to substantially increase the viscosity, more detailed measurements of viscosity were made using the Rheometrics ARES.

3.4 Results 3.4a Screening in Fabric Softeners

For the commercially available Unilever products, Unilever supplied us with some base material. However, it quickly became apparent that it would not be easy to determine if the chemistries were compatible in the formulation and in particular caused phase separation, since the Unilever formulations are not transparent. Therefore, some work was done with the only transparent fabric softener, Downey Fabric Enhancer, commercially available from Procter & Gamble Co. It was understood from the outset that P&G proprietary technology had made it possible to make a transparent fabric softener, and that the transparency likely hinged on the careful balance of the ingredients. Thus, whether a chemistry rendered the Downey Fabric Enhancer cloudy could not be the only indication of whether or not a chemistry would be compatible in a fabric softener. However, it was thought to be a good starting point, moreover, it was thought that if something could be found that did not cloud Downey Fabric Enhancer, but did increase the viscosity that it would have commercial value.

In addition to the four commercial products, RHODAQUAT T diluted to 10% active was also used as a screening formulation because it enabled screening in a controlled formulation. Below is a brief summary of the findings from the screening of chemistries at 1%. In the table, the rating is based upon a visual observation and the scale is from 1 to 6, where the control is rated a 3, 1 is considered much less viscous than the control, 5 is considered much more viscous than the control, and 6 is considered to be almost a gel. Hatch marks in the box indicate that the formulation did not appear completely compatible.

TABLE 5

Fabric Softener Screening

| Chemistry | RHODAQUAT T @ 10% pH adj | Rating | Downey FE pH adj | Rating | Unilever base pH adj | Rating | Comfort pH adj | Rating | ROBIJN pH adj | Rating |
|---|---|---|---|---|---|---|---|---|---|---|
| Random | | | | | | | | | | |
| VP:MAPTAC (1:9) | N | 3 | | | | | | | | |
| VP:MAPTAC (3:7) | N | 3 | | | | | | | | |
| PAA:MAPTAC (1:9) | N | 3 | | | | | | | | |
| PAA:MAPTAC | Y | 3 | | | | | | | | |
| VP:PADAMQUAT (50 k/10 k) | N | 3 | | | | | | | | |
| HEA:DADMAC (1:9) | N | 3 | | | | | | | | |
| CLA-STA FS | N | 3 | N | 3.5 | | | Y | 4 | N | 4 |
| ALKAFLOC EC-752M | N | 6 | N | 3 | | | N | 4.5 | N | 5 |
| PAA w/PEO-grafts (01VTA105) | Y | 2.5 | | | | | | | | |
| VP:DMAPMA:C18 DIQUAT (47.5:47.5:5) | NA | gel | NA | gel | | | NA | gel | NA | gel |
| Block Copolymers | | | | | | | | | | |
| PAA:PAM (1 k/10 k) | N | 2 | | | | | | | | |
| PAA:PAM(1 k/1 k) | Y | 2 | | | | | | | | |
| PAA:PAM(1 k/5 k) | Y | 2 | | | | | | | | |
| VP:PADAMQUAT (50 k/10 k) | N | 2.5 | | | | | | | | |

TABLE 5-continued

Fabric Softener Screening

| | RHODAQUAT T | | | | Unilever base | | Comfort | | ROBIJN | |
| | @ 10% | | Downey FE | | pH | | pH | | pH | |
| Chemistry | pH adj | Rating | pH adj | Rating | adj | Rating | adj | Rating | adj | Rating |
|---|---|---|---|---|---|---|---|---|---|---|
| Misc. Rhodia Technologies | | | | | | | | | | |
| Jaguar HP 105 | | | | | N | 4 | | | | |
| VES (XE-90-C22 betaine | Y | 2.5 | | | | | | | | |
| Competitor Products | | | | | | | | | | |
| Alcogum L-511 | Y | 6 | | | Y | 3.5 | | | | |
| Alcogum L-520 | Y | 6 | | | Y | 3.5 | | | | |
| Acrysol RM-825 | | | | | N | 3 | | | | |
| SNF DP-200 | | | | | | | N | 5 | N | 5 |
| 3V Sigma CN | N | 6 | N | 3 | | | N | 6 | NA | Gel |
| 3V Sigma CR | N | 6 | N | 3 | | | NA | gel | N | 6 |

Based upon these findings, it became apparent that the VP:DMAPMA:C18 DIQUAT showed great potential, since at 1% it already made a gel of the fabric softeners. In order to continue these studies it was concluded that the polymer should be tested at other concentration levels. In addition, modifications were attempted in the synthesis in order to make it more dispersible.

Realizing that there was an equal need for thickening of acidic toilet bowl formulations, further screening of potential candidates was additionally carried out in a toilet bowl formulation supplied directly by Clorox.

IV. VP:DMAPMA:C18 DIQUAT

The VP:DMAPMA:C18 DIQUAT (47.5:47.5:5) polymer was designed so as to act as a thickener at low pH. The presence of the hydrophobically modified diquaternary monomer (hereinafter "DIQUAT") is meant to create interactions which allow for the polymer to create a sort of crosslinked structure in aqueous solution. At low pH, the hydrophobic interactions are balanced by the hydrophilicity of the polymer coming from the charged DMAPMA. The presence of VP insures that the polymer remains hydrophilic enough at low pHs so as to keep the polymer water soluble. Depending on the synthesis route chosen it was found that certain samples had more or less of a problem becoming dispersed in water, and moreover that the pH of the water could also play a role. With all this in mind, the polymer samples of VP:DMAPMA:C18 DIQUAT were initially screened in water at various pHs to identify the most promising candidates. Of the samples tested, two samples: R0376-2 and R0376-8 appeared the most promising and were selected for further testing in the various formulas. As it had already been determined that addition of VP:DMAPMA:C18 DIQUAT at 1% in the fabric softeners was too high, subsequent testing was tried at lower concentrations. The four following charts show the effect of the addition of R0376-2 and R0376-8 at 0.5% in the Clorox toilet bowl cleaner base, Unilever fabric softener base, ROBIJN, and Comfort.

Lower levels of R0376-2 and R0376-8 were also studied, specifically at 0.05%, 0.1%, and 0.3% in the formulations. In the case of Comfort, R0376-2 gave stepwise improvement in viscosity with increasing concentration. This was not the case, however, with ROBIJN which gave some strange results. There was no benefit observed using R0376-8 in either of the products at concentrations less than 0.5%.

4.1 Polymer Comparisons to VP:DMAPMA:C18 DIQUAT

Based upon the favorable results found using VP:DMAPMA:C18 DIQUAT it was of interest to benchmark it against other polymer chemistries. Based upon the screening done earlier on purely visual assessments, benchmark comparisons of VP:DMAPMA:C18 DIQUAT were made against Rhodia's ALKAFLOC EC-752M, as well as some competitive commercially available polymers. It should be noted that ALKAFLOC EC-752M is a lightly crosslinked copolymer of acrylamide:dimethylaminoethyl-methacrylate methyl chloride quaternary (METAC), which due to the manner in which it is synthesized, is produced as a water in oil emulsion.

The ALKAFLOC EC-752M was found to be incompatible when added directly into the aqueous formulations as it was received. Therefore, in order to test the ALKAFLOC EC-752M in the various formulas, the product was extracted by adding it to acetone which caused the polymer to precipitate out of solution. The acetone and emulsion mixture was then filtered to isolate the polymer. SNF Floerger's DP200 was said to be a competitor to ALKAFLOC EC-752M, however, it was supplied in a form which allowed it to be used directly.

Figure 1:
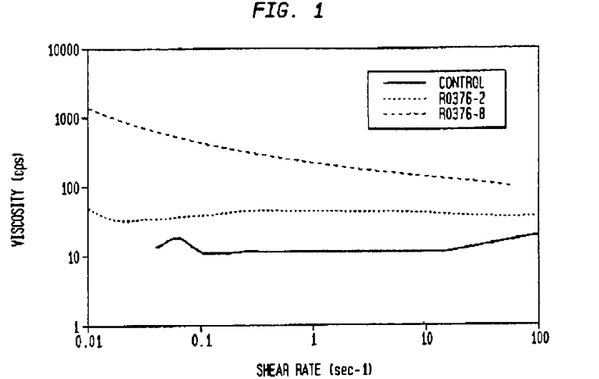
FIG. 1 is viscosity profile of Clorox toilet bowl cleaner base compared to the base with 0.5% R0376-2 and R0376-8.
Figure 2:
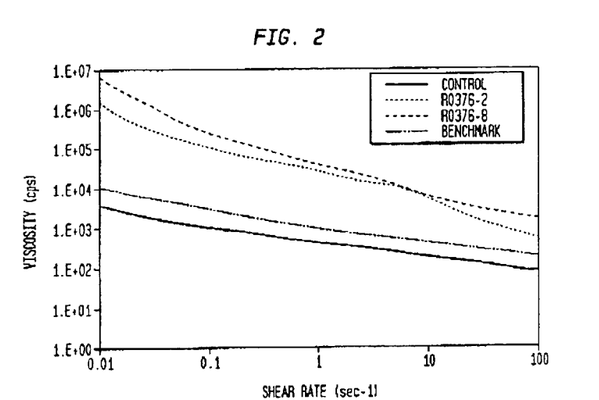
FIG. 2 is a viscosity profile of Unilever fabric softener base compared to the base with 0.5% R0376-2 and R0376-8, and compared to a benchmark supplied by Unilever.
Figure 3:
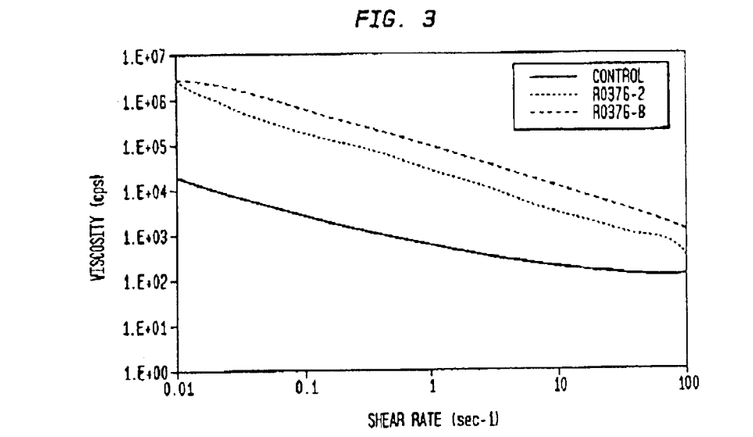
FIG. 3 is a viscosity profile of ROBIJN fabric softener with and without 0.5% R0376-2 and R0376-8.
Figure 4:
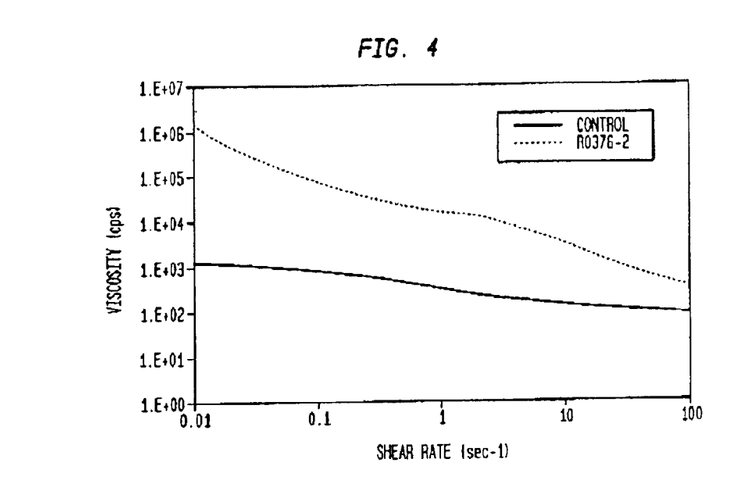
FIG. 4 is a viscosity profile of Comfort fabric softener with and without 0.5% R0376-2.
Figure 5:
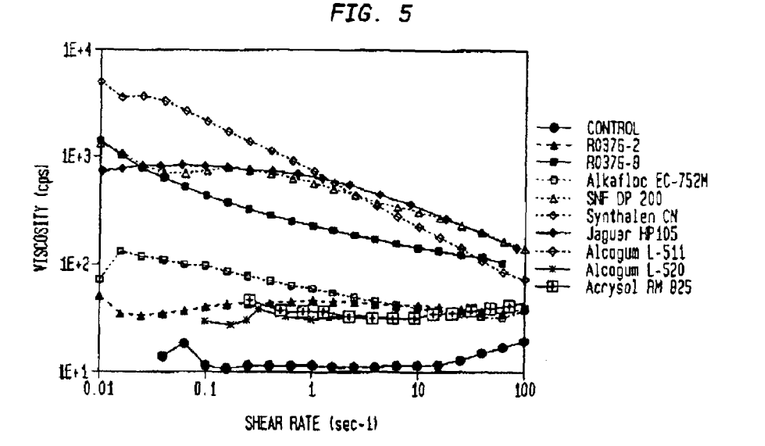
FIG. 5 is a viscosity profile of Clorox toilet bowl cleaner base with and without R0376-2 and R0376-8 at 0.5% as compared to some other commercially available polymers.

As the viscosity profile of FIG. 5 shows, the SYNTHALEN CN (commercially available from CV3 Sigma) enhanced the viscosity of the Clorox toilet bowl cleaner base formula the most. The SYNTHALEN CN product is believed to be a crosslinked cationic homopolymer of cationic monomers, and is advertised to be effective in thickening cationic surfactant solutions. (1–4) The SNF Floerger's DP200 product which was suggested to be based on a chemistry similar to the ALKAFLOC EC-752M was slightly better than all of Rhodia's technology including the ALKA-FLOC EC-752M. Acrysol RM-825 which was cited in a Unilever patent (5) to be a Rohm and Haas polyurethane polymer capable of thickening fabric softeners, did not have any significant affect on the toilet bowl formula base.

Figure 6:
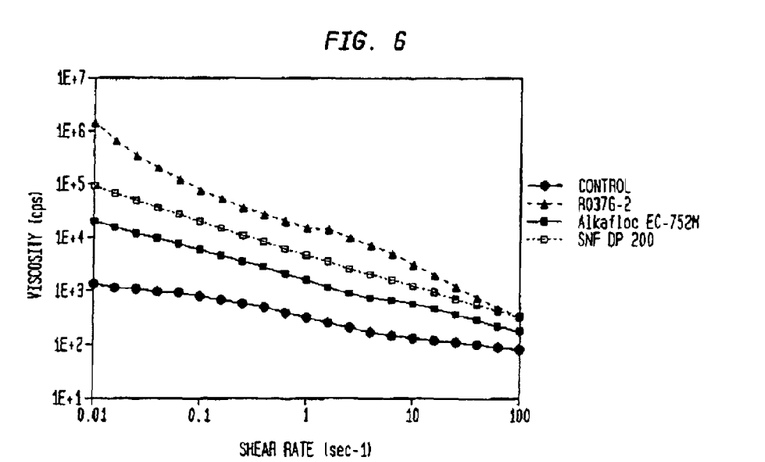
FIG. 6 is a viscosity profile of Comfort with and without R0376-2 at 0.5% as compared to some other commercially available polymers.
Figure 7:
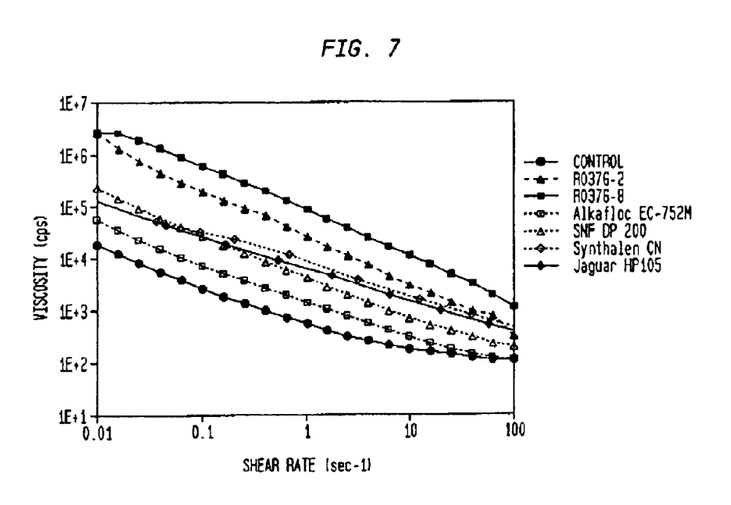
FIG. 7 is a viscosity profile of ROBIJN with and without R0376-2 at 0.5% as compared to some other commercially available polymers.

In the case of the fabric softeners, the results were rather different, where the biggest increase in viscosity was achieved by using the VP:DMAPMA:C18 DIQUAT. (FIGS. 6 and 7) It is not clear why there is a difference in level of performance coming from the different chemistries in toilet bowl formulations as opposed to fabric softener formulations. However, while both types of formulations have low pHs and contain quaternary surfactants, clearly there are two significant differences between the formulations: 1) the level of quaternary surfactant and 2) the level of solvent. For the toilet bowl cleaner base the level of quaternary surfactant is less that 1 wt % and there is relatively little solvent, while in the case of the fabric softeners, the level of quaternary can be as high as 10 wt % or higher, and contain a large amount of solvent. As most of the polymers tested were cationic polymers, interactions with the quaternary surfactant should have been minimal. Possibly then, it was due to the high level of solvent in the fabric softeners as opposed to toilet bowl cleaners, which allowed the VP:DMAPMA:C18 DIQUAT to show such good performance. It had been noticed that some of the lots of VP:DMAPMA:C18 DIQUAT which had been made were very difficult if not impossible to disperse in water, which was assumed to be due to the manner in which the C18 had been incorporated into the polymer. Thus, perhaps the higher level of solvent facilitated the polymer to become more fully extended.

What is claimed is:

1. A hydrophobic modified copolymer having the formula:

wherein X is selected from O, NH, or NR; Y is any alkyl, alkylene with or without heteroatoms, and $R^{0, R1}$, $R^2$ $R^3$, $R^4$, which are identical or different, are selected from C1–C4 alkyl groups, R is selected from any alkyl group with or without heteroatoms, and $R^5$ is a hydrphobe having an alkyl chain or more than 4 atoms.

2. A process for synthesizing the copolymer compound of claim 1 comprising the following reaction scheme:

wherein R is selected from $C_{12}H_{23}$ or $C_{18}H_{37}$ and X is selected from ethylene and propylene.

3. The process of claim 2 comprising suspension polymerization in an aqueous sodium carbonate, bicarbonate, or combination thereof.

4. An acidic home care formulation having a pH of 4 or below comprising a copolymer derived from one or more hydrophobic modified quaternary monomers said copolymer having the formula wherein R is selected from $C_{12}H_{23}$ or $C_{18}H_{37}$ and X is selected from ethylene and propylene.

5. The formulation of claim 4 wherein said monomer is a thickening agent.

6. The formulation of claim 4 wherein said home care formulation is a toilet bowl cleaner or a fabric softener.

7. A quaternary surfactant containing formulation comprising a rheology modifying agent, said rheology modifying agent comprising a hydrophobic modified diquaternary monomer or a copolymer wherein said copolymer has the formula:

wherein R is selected from $C_{12}H_{23}$ or $C_{18}H_{37}$ and X is selected from ethylene and propylene.

* * * * *